United States Patent [19]

Grollier et al.

[11] Patent Number: 4,761,273

[45] Date of Patent: Aug. 2, 1988

[54] COMPOSITION IN THE FORM OF AN AEROSOL FOAM, BASED ON A CATIONIC POLYMER AND AN ANIONIC POLYMER

[75] Inventors: Jean F. Grollier, Paris; Annie Madrange, Saint Germain en Laye; Michele Chailley, Fontenay sous Bois, all of France

[73] Assignee: L'Oreal, Paris, France

[21] Appl. No.: 758,409

[22] Filed: Jul. 24, 1985

Related U.S. Application Data

[63] Continuation of Ser. No. 614,400, May 29, 1984, abandoned, which is a continuation of Ser. No. 376,126, May 7, 1982, abandoned.

[30] Foreign Application Priority Data

May 8, 1981 [LU] Luxembourg .......................... 83349

[51] Int. Cl.$^4$ ...................... A61K 7/06; A61K 7/11; A61K 9/12
[52] U.S. Cl. ........................................... 424/47; 424/70
[58] Field of Search ...................................... 424/47, 70

[56] References Cited

U.S. PATENT DOCUMENTS

| | | | |
|---|---|---|---|
| 3,420,703 | 1/1969 | Kirschnek et al. | 117/139.5 |
| 3,549,542 | 12/1970 | Holderby | 252/137 |
| 3,917,817 | 11/1975 | Vanlergerghe et al. | 424/70 |
| 3,958,581 | 5/1976 | Abegg et al. | 132/7 |
| 3,969,500 | 7/1976 | Kennerley | 424/10 |
| 4,013,787 | 3/1977 | Vanlerberghe et al. | 424/70 |
| 4,126,674 | 11/1978 | Mausner | 424/31 |
| 4,197,865 | 4/1980 | Jacquet et al. | 132/7 |
| 4,217,914 | 8/1980 | Jacquet et al. | 132/7 |
| 4,240,450 | 12/1980 | Grollier et al. | 132/7 |
| 4,402,977 | 9/1983 | Grollier et al. | 424/70 |
| 4,445,521 | 5/1984 | Grollier et al. | 132/7 |

FOREIGN PATENT DOCUMENTS

| | | | |
|---|---|---|---|
| 2310283 | 9/1963 | Fed. Rep. of Germany | 424/70 |
| 1469348 | 9/1969 | Fed. Rep. of Germany | 424/70 |
| 2324797 | 11/1973 | Fed. Rep. of Germany | 424/70 |
| 3044754 | 6/1981 | Fed. Rep. of Germany | 424/70 |
| 2184890 | 12/1973 | France | 424/70 |
| 2270846 | 12/1975 | France | 424/70 |
| 2280361 | 2/1976 | France | 424/70 |
| 2316271 | 1/1977 | France | 424/70 |
| 2383660 | 10/1978 | France | 424/70 |
| 422408 | 3/1982 | Sweden | 424/70 |
| 993181 | 5/1965 | United Kingdom | 424/78 |
| 1133881 | 11/1968 | United Kingdom | 424/47 |
| 1356395 | 6/1974 | United Kingdom | 424/47 |
| 1364967 | 8/1974 | United Kingdom | 424/78 |
| 1424002 | 2/1976 | United Kingdom | 424/70 |
| 1545297 | 5/1979 | United Kingdom | 424/70 |
| 2025228 | 1/1980 | United Kingdom | 424/70 |
| 2063671 | 6/1981 | United Kingdom | 424/70 |

OTHER PUBLICATIONS

Ash et al., A Formulary of Cosmetic Preparations, 1977, pp. 138 & 144.
Wiley-Interscience, "Cosmetics Science and Technology", 6/5/69, pp. 98–100, Balsam, Rieger, Sagarin, Gershon and Strianse.
B. F. Goodrich Brochure: "Carbopol Water Soluble Resins", (Code GC-67).
B. F. Goodrich Publication: "Carbopol Resins, Newsletter No. 6", (Code 7406).
B. F. Goodrich Brochure: "Personal Care Products, Carbopole Resins", (Code GC-68).
Lang, "New Techniques for Using Carbopol Resins and Moisturizing Lotions", Cosmetics and Perfumery, Mar. 1974.
B. F. Goodrich Brochure: "Carbopole Water-Soluble Resins, Formulary", Issue No. 1, (Code 6611).
Dow Corning EF-13574B Cationic Emulsion (Cosmetic Use), Dow Corning Corporation, Oct. 12, 1970.

*Primary Examiner*—Dale R. Ore
*Attorney, Agent, or Firm*—Fleit, Jacobson, Cohn & Price

[57] ABSTRACT

The invention provides a pressurized composition based on cationic and anionic polymers and containing at least one cationic polymer and/or one anionic polymer which foams in aqueous solution, in an aqueous solvent medium such that, in the atmosphere, the composition forms an unstable foam on contact with the hair.

39 Claims, No Drawings

COMPOSITION IN THE FORM OF AN AEROSOL FOAM, BASED ON A CATIONIC POLYMER AND AN ANIONIC POLYMER

This is a continuation of application Ser. No. 614,400, filed May 29, 1984, which is a continuation of Ser. No. 376,126 filed, May 7, 1982, both now abandoned.

This invention relates to compositions based on anionic and cationic polymers and dispensed in the form of an aerosol foam intended for use in the treatment of the hair.

As used herein, the description "aerosol foam" denotes a foam obtained from a composition packaged in pressurised form.

The use of compositions based on cationic polymers and anionic polymers has already been described, in particular in French Specification No 2 383 660. These compositions make it possible, in particular, to obtain an easy comb-out and a pleasant feel on wet hair and shine and a good hold of the hair style on dry hair.

Various embodiments are envisaged in the said specification for applying the compositions to the keratin to be treated. We have now discovered, according to the present invention, that the application of the compositions in the form of an aerosol foam makes it possible to obtain a better distribution, easier use, a saving of product and superior results from the cosmetic point of view, in particular compared with the lotions described previously.

We have discovered, in particular, that it is possible to prepare a foam possessing these properties by using solely a cationic polymer, an anionic polymer and an aqueous solvent medium, without the need to add surface-active compounds possessing foaming properties.

By this means it is also possible to reduce the amount of propellant which can be used, and also the respirable volume of the usual formulations of polymers in the form of sprays from an aerosol pack.

We have discovered, more particularly, that the choice of certain cationic or anionic polymers having foaming properties makes it possible, in combination with the solvent medium used, to obtain a very unstable foam which disappears rapidly on contact with the head of hair, without leaving residual foam which it would seem desirable to remove by rinsing. Furthermore, this foam, which can be left on the hair without rinsing, detracts neither from the harmlessness, nor the appearance and the cosmetic properties of the dried hair.

The present invention thus provides a pressurised composition based on cationic and anionic polymers, under conditions such that it forms a very unstable foam on contact with the hair, as well as a process for the preparation of a very unstable foam based on cationic and anionic polymers and to a process for the treatment of the hair with the aid of such a composition.

The cationic and anionic polymers which can be used according to the invention are in themselves well known and are chosen, in the case of the cationic polymers, from amongst polymers containing primary, secondary, tertiary and/or quaternary amine groups, generally having a molecular weight of 500 to 5,000,000, and, more particularly, polymers for the polyamine, polyaminopolyamide and poly-(quaternary ammonium) type in which the amine or ammonium group forms part of the polymer chain or is joined thereto.

Amongst these polymers, there may be mentioned, more particularly:

(1) Vinylpyrrolidone/dialkylaminoalkyl acrylate or methacrylate copolymers (quaternised or unquaternised), such as those sold under the name Gafquat by the Gaf Corp, for example "copolymer 845" and Gafquat 734 or 755, described in greater detail in particular in French Pat. No. 2 077 143.

(2) Cellulose ether derivatives containing quaternary ammonium groups, such as those described in French Pat. No. 1 492 597 and especially the polymers sold under the name JR, such as JR 125, JR 400 and JR 30 M, and under the name LR, such as LR 400 and LR 30 M, by the Union Carbide Corp, and cationic cellulose derivatives, such as the products sold under the name CELQUAT L 200 and CELQUAT H 100 by National Starch and described in U.S. Pat. No. 4,131,576.

(3) Cationic polysaccharides, such as those described in U.S. Pat. Nos. 3,589,978 and 4,031,307, and in particular Jaguar C 13 S sold by Meyhall.

(4) Cationic polymers chosen from the group comprising:

(a) polymers containing units of the formula:

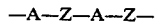 (I)

in which A denotes a radical containing two amino groups, preferably a piperazinyl radical, and Z denotes the symbol B or B'; B and B', which are identical or different, denote a divalent radical which is a straight-chain or branched-chain alkylene radical which contains up to, say, 7 consecutive carbon atoms in the main chain, is unsubstituted or substituted by one or more hydroxyl groups and can also contain one or more oxygen, nitrogen and sulphur atoms and 1 to 3 aromatic and/or heterocyclic rings, the oxygen, nitrogen and sulphur atoms generally being present in the form of an ether or thioether, sulphoxide, sulphone, sulphonium, amine, alkylamine, alkenylamine, benzylamine, amine oxide, quaternary ammonium, amide, imide, alcohol, ester and/or urethane group; these polymers and their preparation are described in French Pat. No. 2 162 025;

(b) polymers containing units of the formula:

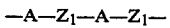 (II)

in which A denotes a radical containing two amino groups, preferably a piperazinyl radical, and $Z_1$ denotes the symbol $B_1$ or $B'_1$ while denoting the symbol $B'_1$ at least once; $B_1$ denotes a divalent radical which is a straight-chain or branched-chain alkylene or hydroxyalkylene radical having up to, say, 7 consecutive carbon atoms in the main chain, and $B'_1$ is a divalent radical which is a straight-chain or branched-chain alkylene radical which has up to, say, 7 consecutive carbon atoms in the main chain, is unsubstituted or substituted by one or more hydroxyl radicals and is interrupted by one or more nitrogen atoms, the nitrogen atom being substituted by an alkyl chain having from 1 to 4 carbon atoms, preferably 4 carbon atoms, which is optionally interrupted by an oxygen atom and optionally contains one or more hydroxyl groups; the polymers of the formula (II) and their preparation are described in French patent application No. 2 280 361; and (c) the alkylation products, with alkyl and benzyl halides or lower (generally of 1 to 6 carbon atoms) alkyl tosylates or mesylates, and the oxidation products, of the polymers of the formulae (I) and (II) indicated above under (a) and (b).

(5) Optionally alkylated and crosslinked polyamino-amides chosen from at least one crosslinked polymer obtained by crosslinking a polyamino-polyamide (A) prepared by the polycondensation of an acid compound with a polyamine. The acid compound is chosen from (i) organic dicarboxylic acids, (ii) aliphatic monocarboxylic and dicarboxylic acids containing a double bond, (iii) esters of the abovementioned acids, preferably the esters with lower alkanols having from 1 to 6 carbon atoms, and (iv) mixtures of these compounds. The polyamine is a bis-primary or mono- or bis-secondary polyalkylene-polyamine; up to 40 mol% of this polyamine can be replaced by a bis-primary amine, preferably ethylenediamine, or by a bis-secondary amine, preferably piperazine, and up to 20 mol% can be replaced by hexamethylenediamine. The crosslinking is carried out by means of a crosslinking agent (B) chosen from epihalogenohydrins, diepoxides, dianhydrides, unsaturated anhydrides and bis-saturated derivatives, in proportions of 0.025 to 0.35 mol of crosslinking agent per amine group of the polyamino-polyamide (A). These polymers and their preparation are described in greater detail in French Pat. No. 2 252 840.

The alkylation can be carried out with, say, glycidol, ethylene oxide, propylene oxide or acrylamide.

The polyamino-polyamides (A) themselves can also be used according to the invention.

(6) Crosslinked polyamino-polyamides obtained by crosslinking a polyamino-polyamide (A, described above) by means of a crosslinking agent which is:

(I) compounds chosen from (1) bis-halogenohydrins, (2) bis-azetidinium compounds, (3) bis-halogenoacyl-diamines and (4) bis-(alkyl halides);

(II) oligomers obtained by reacting a compound (a) chosen from the group comprising (1) bis-halogenohydrins, (2) bis-azetidinium compounds, (3) bis-halogenoacyl-diamines, (4) bis-(alkyl halides), (5) epihalogenohydrins, (6) diepoxides and (7) bis-unsaturated derivatives, with a compound (b) which is a difunctional compound which is reactive towards the compound (a); and (III) the quaternisation product of a compound chosen from the compounds (I) and the oligomers (II) and containing one or more tertiary amine groups which can be totally or partially alkylated with an alkylating agent (c) preferably chosen from methyl or ethyl chlorides, bromides, iodides, sulphates, mesylates and tosylates, benzyl chloride or bromide, ethylene oxide, propylene oxide and glycidol, the crosslinking being carried out by means of 0.025 to 0.35 mol, in particular of 0.025 to 0.2 mol and more particularly of 0.025 to 0.1 mol, of crosslinking agent per amine group of the polyamino-polyamide.

These crosslinking agents and these polymers, together with the process for their preparation, are described in French application No. 2,368,508.

(7) Polyamino-polyamide derivatives resulting from the condensation of a polyalkylene-polyamine with a polycarboxylic acid, followed by alkylation by means of difunctional agents, such as the adipic acid/dialkylaminohydroxyalkyl-dialkylenetriamine copolymers in which the alkyl radical contains 1 to 4 carbon atoms and preferably denotes methyl, ethyl or propyl, which are described in French Pat. No. 1,583,363.

The products which make it possible to obtain particularly valuable results are the adipic acid/dimethylaminohydroxypropyl-diethylenetriamine copolymers sold under the name Cartarétine F, F$_4$ or F$_8$ by SANDOZ.

(8) Polymers obtained by reacting a polyalkylene-polyamine containing two primary amine groups and at least one secondary amine group, with a dicarboxylic acid chosen from diglycolic acid and saturated aliphatic dicarboxylic acids having 3 to 8 carbon atoms, the molar ratio of the polyalkylene-polyamine to the dicarboxylic acid being from 0.8:1 to 1.4:1, and the resulting polyamide being reacted with epichlorohydrin in a molar ratio of epichlorohydrin to the secondary amine groups of the polyamide of from 0.5:1 to 1.8:1; these polymers are mentioned in U.S. Pat. Nos. 3,227,615 and 2,961,347.

Particularly valuable polymers are those sold under the name HERCOSETT 57 by Herculès Incorporated, and that sold under the name PD 170 or DELSETTE 101 by Herculès, in the case of the adipic acid/epoxypropyl-diethylenetriamine copolymer.

(9) Cyclic polymers generally having a molecular weight of 20,000 to 3,000,000, such as homopolymers containing, as the main constituent of the chain, units corresponding to the formula (III) or (III')

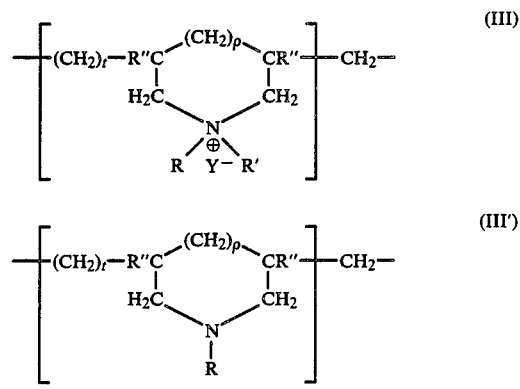

in which p and t are equal to 0 or 1, and $p+t=1$, R'' denotes hydrogen or methyl, R and R' independently of one another denote an alkyl group having from 1 to 22 carbon-atoms, a hydroxylalkyl group in which the alkyl group preferably has 1 to 5 carbon atoms, or a lower amidoalkyl group, and R and R' can denote, together with the nitrogen atom to which they are attached, heterocyclic groups such as piperidinyl or morpholinyl, and $Y^\ominus$ is an anion, such as bromide, chloride, acetate, borate, citrate, tartrate, bisulphate, bisulphite, sulphate or phosphate, and also copolymers containing units of the formula III or III' and, preferably, units derived from acrylamide or from diacetoneacrylamide.

Amongst the quaternary ammonium polymers of the type defined above, those which are more particularly preferred are the dimethyldiallylammonium chloride homopolymer sold under the name MERQUAT 100 and having a molecular weight of less than 100,000, and the dimethyldiallylammonium chloride/acrylamide copolymer having a molecular weight of more than 500,000 and sold under the name MERQUAT 550 by MERCK.

These polymers are described in French Pat. No. 2,080,759 and its certificate of addition No. 2,190,406.

(10) Poly-(quaternary ammonium) compounds of the formula

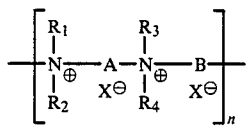 (IV)

in which $R_1$ and $R_2$, and $R_3$ and $R_4$, which are identical or different, represent aliphatic, alicyclic or arylaliphatic radicals containing a maximum of 20 carbon atoms, or lower hydroxyaliphatic radicals, or alternatively $R_1$ and $R_2$, and $R_3$ and $R_4$, together or separately form, with the nitrogen atoms to which they are attached, heterocyclic rings optionally containing a second hetero-atom other than nitrogen, or alternatively $R_1$, $R_2$, $R_3$ and $R_4$ represent a group

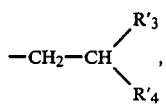

$R'_3$ denoting hydrogen or lower alkyl and $R'_4$ denoting SO,

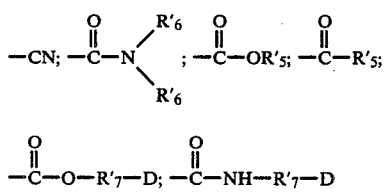

$R'_5$ denoting lower alkyl, $R'_6$ denoting hydrogen or lower alkyl, $R'_7$ denoting alkylene and D denoting a quaternary ammonium group; A and B independently represent a polymethylene group containing from 2 to 20 carbon atoms, which can be linear or branched and saturated or unsaturated and can contain, inserted in the main chain, one or more aromatic rings, such as the group

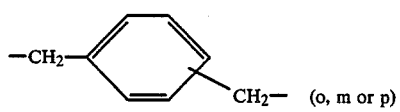

or one or more groups $-CH_2-Y-CH_2-$, Y denoting O, S, SO,

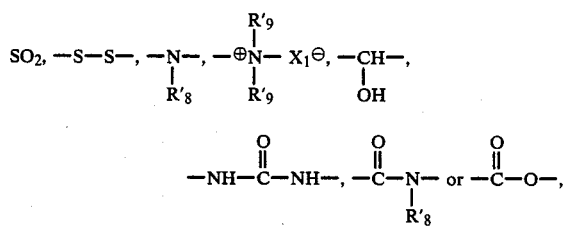

$X_1^\ominus$ denoting an anion derived from a mineral or organic acid, $R'_8$ denoting hydrogen or lower alkyl and $R'_9$ denoting lower alkyl, or alternatively A and $R_1$ and $R_3$ form a piperazine ring with the two nitrogen atoms to which they are attached; moreover, if A denotes a linear or branched, saturated or unsaturated alkylene or hydroxyalkylene radical, B can also denote a group:

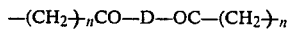

in which D denotes:
(a) a glycol radical of the formula $-O-Z-O-$, in which Z denotes a linear or branched hydrocarbon radical or a group corresponding to the formulae

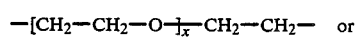

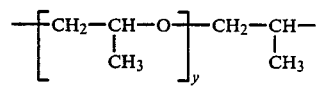

in which x and y denote an integer from 1 to 4, representing a definite and unique degree of polymerisation (or any number from 1 to 4, representing an average degree of polymerisation in the case of a mixture);
(b) a bis-secondary diamine radical, such as a piperazine derivative;
(c) a bis-primary diamine radical of the formula: $-NH-Y-NH-$, in which Y denotes a linear or branched hydrocarbon radical or the divalent radical $-CH_2-CH_2-S-S-CH_2-CH_2-$; or
(d) a ureylene group of the formula $-NH-CO-NH-$; n is such that the molecular weight is generally between 1,000 and 100,000; and $X^-$ denotes an anion.

Polymers of this type are described, in particular, in French Pat. Nos. 2,320,330 and 2,270,846, French application Nos. 2,316,271, 2,336,434 and 2,413,907 and U.S. Pat. Nos. 2,273,780, 2,375,853, 2,388,614, 2,454,547, 3,206,462, 2,261,002 and 2,271,378.

Other polymers of this type are described in U.S. Pat. Nos. 3,874,870, 4,001,432, 3,929,990, 3,966,904, 4,005,193, 4,025,617, 4,025,627, 4,025,653, 4,026,945 and 4,027,020.

(11) Homopolymers or copolymers derived from acrylic or methacrylic acid and containing at least one unit:

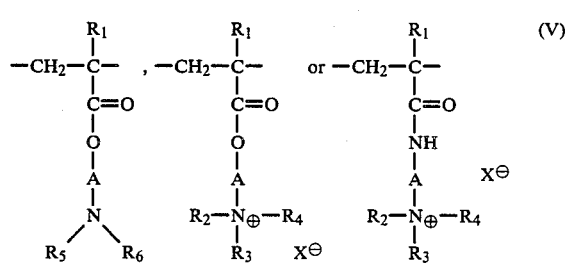 (V)

in which $R_1$ is H or $CH_3$, A is a linear or branched alkyl group having 1 to 6 carbon atoms or a hydroxyalkyl group having 1 to 4 carbon atoms, $R_2$, $R_3$ and $R_4$, which are identical or different, denote an alkyl group having 1 to 18 carbon atoms or a benzyl group, $R_5$ and $R_6$ denote H or alkyl having 1 to 6 carbon atoms and X denotes methosulphate or halide, such as chloride or bromide.

The comonomer or comonomers which can be used typically belong to the family comprising: acrylamide, methacrylamide, diacetone-acrylamide, acrylamide and methacrylamide substituted on the nitrogen by one or more lower alkyls, alkyl esters of acrylic and methacrylic acids, vinylpyrrolidone and vinyl esters.

By way of example, there may be mentioned:

the products listed under the names Quaternium 38, 37, 49 and 42 in the Cosmetic Ingredient Dictionary, the acrylamide/beta-methacryloyloxyethyl-trimethylammonium methosulphate copolymers sold under the names Reten 205, 210, 220 and 240 by Herculès, the aminoethylacrylate phosphate/acrylate copolymer sold under the name Catrex by National Starch, and the crosslinked graft cationic copolymers having a molecular weight of 10,000 to 1,000,000, and preferably of 15,000 to 500,000, and resulting from the copolymerisation of:

(a) at least one cosmetic monomer,
(b) dimethylaminoethyl methacrylate,
(c) polyethylene glycol and
(d) a polyunsaturated crosslinking agent, these copolymers being described in French Pat. No. 2,189,434.

(12) Quaternary polymers of vinylpyrrolidone and of vinylimidazole, such as LUVIQUAT FC 905 sold by BASF.

(13) Cationic silicone polymers, such as those described in European application Nos. 17,121 and 17,122, U.S. Pat. No. 4,185,087, Japanese Patent Application No. 80/66,506 and Austrian patent application No. 71/01,171, or also those mentioned in the CTFA dictionary under the name AMODIMETHICONE, such as the product marketed as a mixture with other ingredients under the name "DOW CORNING 929 cationic emulsion".

Other cationic polymers which can be used are polyalkyleneimines, in particular polyethyleneimines, polymers containing vinylpyridine units or vinylpyridinium units in the chain, condensates of polyamines and of epichlorohydrin, poly-(quaternary ureylenes) and chitin derivatives.

The anionic polymers are polymers containing units derived from a carboxylic, sulphonic or phosphoric acid and usually have a molecular weight of 500 to 5,000,000. These polymers are water-soluble polymers, it being possible for this solubility to be obtained by neutralisation of the acid groups with an alkali, such as sodium hydroxide, potassium hydroxide, ammonia or an amine, like mono-, di- or tri-ethanolamine, 2-amino-2-methylpropanol or 2-amino-2-methylpropane-1,3-diol, mono-, di- or tri-ethylamine, mono-, di- or tri-propylamine or isopropylamine.

The carboxylic acid groups can be provided by unsaturated monocarboxylic or dicarboxylic acids, such as those corresponding to the formula:

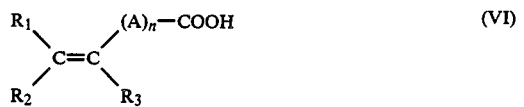

(VI)

in which n is 0 or an integer from 1 to 10, A denotes a methylene group optionally joined to the carbon atom of the unsaturated group, or to the adjacent methylene group in the case where n is greater than 1, via a heteroatom, such as oxygen or sulphur, $R_1$ denotes a hydrogen atom or a phenyl or benzyl group, $R_2$ denotes a hydrogen atom, a lower alkyl group or a carboxyl group and $R_3$ denotes a hydrogen atom, a lower alkyl group, a group —$CH_2$—COOH or a phenyl or benzyl group.

In the abovementioned formula, a lower alkyl radical preferably is one having 1 to 4 carbon atoms, in particular methyl or ethyl.

According to the invention, the preferred anionic polymers containing carboxylic acid groups are:

(A) Hompolymers or copolymers of acrylic or methacrylic acid or salts thereof, and, in particular, the products sold under the name VERSICOL E or K by ALLIED COLLOID, under the name ULTRAHOLD 8 by CIBA GEIGY and under the name DARVAN No. 7 by Van der BILT; acrylic acid/acrylamide copolymers sold in the form of their sodium salt under the name RETEN 421, 423 or 425 by HERCULES; and the sodium salts of polyhydroxycarboxylic acids, sold under the name HYDAGEN F by HENKEL.

(B) Copolymers of acrylic or methacrylic acid with a monoethylenic monomer, such as ethylene, styrene, a vinyl or allyl ester or acrylic or methacrylic acid ester, optionally grafted onto a polyalkylene glycol, such as polyethylene glycol, and optionally crosslinked. Polymers of this type are described, in particular, in French Pat. No. 1 222 944 and German Specification No. 2 330 956. Other such copolymers contain an optionally N-alkylated and/or N-hydroxylated acrylamide unit in their chain, such as those described, in particular, in Luxembourg patent application Nos. 75 370 and 75 371, or those sold under the name QUADRAMER 5 by American Cyanamid.

(C) Copolymers derived from crotonic acid, such as those containing, in their chain, vinyl acetate or propionate units and optionally other monomers such as allyl of methallyl esters, a vinyl ether or a vinyl ester of a saturated linear or branched carboxylic acid with a long (generally containing at least 8 carbon atoms) hydrocarbon chain, such as those containing at least 5 carbon atoms, it being possible, if appropriate, for these polymers to be grafted and crosslinked, or also a vinyl, allyl or methallyl ester of an α- or β-cyclic carboxylic acid. Polymers of this type are described, inter alia, in French Pat. Nos. 1 222 944, 1 580 545, 2 265 782, 2 265 781 and 1 564 110 and French Specification No. 2 439 798. Commercial products included in this class are the resins 28-29-30, 26-13-14 and 28-13-10 sold by National Starch.

(D) Polymers derived from maleic, fumaric and itaconic acids or anhydrides with vinyl esters, vinyl ethers, vinyl halides, phenylvinyl derivatives, acrylic acid and its esters; these polymers can be esterified. Polymers of this type are described, in particular, in U.S. Pat. Nos. 2,047,398, 2,723,248 and 2,102,113 and British Pat. No. 839 805. They are in particular those sold under the name GANTREZ AN or ES by General Anilin or under the name EMA 1325 by MONSANTO. Other polymers included in this class are copolymers of maleic, citraconic and itaconic anhydrides with an allyl or methallyl ester optionally containing an acrylamido or methacrylamido group, or with an α-olefine, acrylic or methacrylic acid ester, acrylic or methacrylic acid or vinylpyrrolidone unit in their chain; the anhydride groups can be monoesterified or monoamidified; these polymers are described in French Specification Nos. 76/13 929 and 76/20 917.

(E) Polyacrylamides containing carboxylate groups.

Polymers comprising sulphonic groups include polymers containing vinylsulphonic, styrenesulphonic, lignosulphonic or naphthalenesulphonic units. These polymers are chosen, in particular, from amongst:

Polyvinylsulphonic acid salts having a molecular weight of, say, 1,000 to 100,000, and also copolymers with an unsaturated comonomer, such as acrylic or methacrylic acid or an ester thereof and also substituted or unsubstituted acrylamide or methacrylamide, vinyl esters, vinyl ethers and vinylpyrrolidone.

Polystyrenesulphonic acid salts, such as the sodium salt sold by National STARCH under the name Flexan 500 and having a molecular weight of about 500,000, or the sodium salt sold by National STARCH under the name Flexan 130 and having a molecular weight of about 100,000. Products of this type are described, in particular, in French Pat. No. 2,198,729.

Alkali metal or alkaline earth metal salts of sulphonic acids derived from lignin, and more particularly calcium lignosulphonates or sodium lignosulphonates, such as the product sold under the name Marasperse C-21 by American Can Co. and the $C_{10}$ to $C_{14}$ products sold by Avébène.

Polymers containing salified alkylnaphthalenesulphonic acid units, such as the sodium salt sold under the name Darvan No. 1 by Van der Bilt.

It is also possible to use amphoteric polymers, either with a true cationic polymer or with a true anionic polymer, such as defined above.

The expression "true cationic or anionic polymer" will denote polymers respectively containing solely cationic or solely anionic groups, in contrast to amphoteric polymers containing both cationic and anionic groups.

The amphoteric polymers consist of units A and B randomly distributed in the polymer chain, in which A denotes a unit derived from a monomer containing at least one basic nitrogen atom and B denotes a unit derived from an acid monomer containing one or more carboxylic or sulphonic acid groups, or alternatively A and B can denote groups derived from zwitterionic monomers of carboxybetaine; A and B can also denote a cationic polymer chain containing secondary, tertiary or quaternary amine groups, in which at least one of the amine groups carries a carboxylic or sulphonic acid group joined via a hydrocarbon radical, or alternatively A and B form part of a chain of a polymer containing an alpha,beta-dicarboxyethylene unit in which one of the carboxylic acid groups has been reacted with a polyamine containing one or more primary or secondary amine groups.

These amphoteric polymers are chosen more particularly from:

(1) Polymers resulting from the copolymerisation of a monomer derived from a vinyl compound carrying a carboxylic acid group, such as acrylic acid, methacrylic acid, maleic acid or alpha-chloroacrylic acid, with a basic monomer derived from a substituted vinyl compound containing at least one basic nitrogen atom, such as dialkylaminoalkyl methacrylates and acrylates and dialkylaminoalkyl-methacrylamides and -acrylamides. Compounds of this type are described in U.S. Pat. No. 3,836,537.

(2) Polymers containing units derived from:

(a) at least one monomer chosen from acrylamides or methacrylamides substituted on the nitrogen by an alkyl radical, (b) at least one acid monomer containing one or more reactive carboxylic acid groups, and (c) at least one basic monomer, such as esters of acrylic and methacrylic acids, containing primary, secondary, tertiary and quaternary amine substituents, and the quaternisation product of dimethylaminoethyl methacrylate with dimethyl or diethyl sulphate. These polymers are described in French patent application No. 2,180,006 of National Starch.

(3) The crosslinked polyamino-polyamides described above under (5) and (6), partially or totally alkylated by reaction with acrylic acid, chloroacetic acid or an alkanesultone, and their salts described in Pat. Nos. 2,252,840 and 2,368,508.

(4) Polymers containing zwitterionic units of the formula:

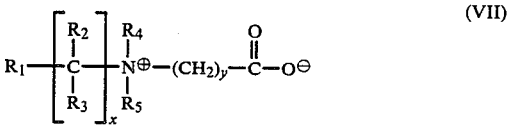

(VII)

in which $R_1$ denotes a polymerisable unsaturated group, such as an acrylate, methacrylate, acrylamide or methacrylamide group, x and y represent an integer from 1 to 3, $R_2$ and $R_3$ represent hydrogen, methyl, ethyl or propyl and $R_4$ and $R_5$ represent a hydrogen atom or an alkyl radical such that the sum of the carbon atoms in $R_4$ and $R_5$ does not exceed 10.

The polymers containing such units can also contain units derived from non-zwitterionic monomers, such as vinylpyrrolidone, dimethylaminoethyl or diethylaminoethyl acrylate or methacrylate or alkyl acrylates or methacrylates, acrylamides or methacrylamides or vinyl acetate.

(5) Polymers derived from chitosan, containing monomeric units corresponding to the following formulae:

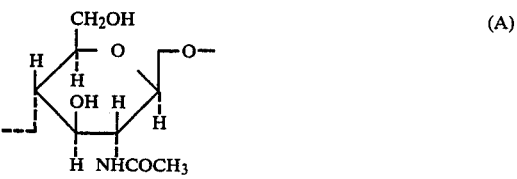

(A)

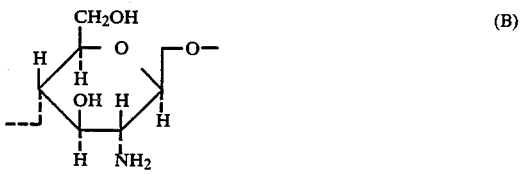

(B)

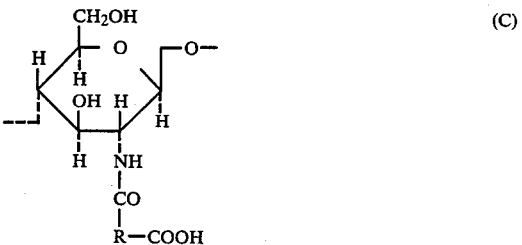

(C)

in which the unit A present in an amount from 0 to 30%, B is present in an amount from 5 to 50% and C is present in an amount from 30 to 90%. In formula C, R represents a radical of the formula:

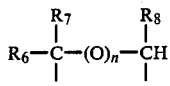

in which n is 0 or 1 such that, if n=0, $R_6$, $R_7$ and $R_8$, which are identical or different, each represent a hydrogen atom, a methyl, hydroxyl, acetoxy or amino radical, a monoalkylamino radical or a dialkylamino radical, optionally interrupted by one or more nitrogen atoms and/or optionally substituted by one or more amine, hydroxyl, carboxyl, alkylthio or sulphonic acid groups, or an alkylthio radical in which the alkyl group carries an amino radical, at least one of the radicals $R_6$, $R_7$ and $R_8$ in this case being hydrogen atom, or if n is equal to 1, $R_6$, $R_7$ and $R_8$ each represent a hydrogen atom, and also the salts formed by these compounds with bases or acids.

(6) The polymers containing units of the formula (VIII) and described in French Pat. Nos. 1,400,366.

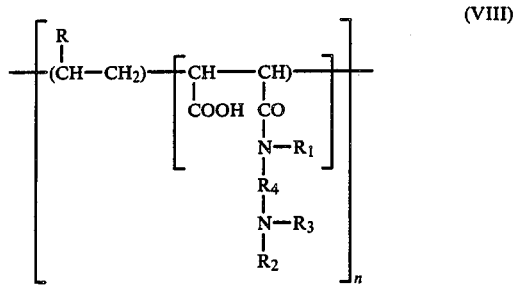

in which R represents a hydrogen atom or a $CH_3O-$, $CH_3CH_2O-$ or phenyl radical, $R_1$ denotes hydrogen or a lower alkyl radical, such as methyl or ethyl, $R_2$ denotes hydrogen or a lower alkyl radical, such as methyl or ethyl, and $R_3$ denotes a lower alkyl radical, such as methyl or ethyl, or a radical corresponding to the formula:

$R_4$ representing a group $-CH_2-CH_2-$, $-CH_2-CH_2-CH_2-$,

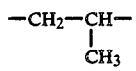

and also the upper homologues of these radicals containing up to 6 carbon atoms.

(7) Amphoteric polymers derived from the cationic polymers described under (4) above, and obtained by reacting chloroacetic acid or sodium chloroacetate with the said compounds.

The present invention provides pressurised compositions based on cationic and anionic polymers, characterised in that at least one of the cationic or anionic polymers foams in water, these polymers being present in a solvent medium containing water, the proportions of water being such that, in the open air, the composition forms an unstable foam on contact with the hair.

According to the invention, the expression "foaming polymer" (a polymer which foams) as used herein is to be understood as meaning a polymer which, in solution in water, gives, according to the Ross Miles test (AFNOR Standard Specification T 73 404 modified as regards the temperature and carried out at 20° C.), a foam height of more than 1 cm and, after pressurisation of the solution, a quality of foam such that its density is less than 0.4 and preferably less than 0.25 g/cm³.

These tests are carried out on compositions prepared in the following manner:

The cationic or anionic polymer is dissolved solely in demineralised water having a resistivity of more than 300,000 ohms$^{-1}$, at a rate of 0.5 g of active ingredient per 100 g of solution if the viscosity is less than 20 cps; if the viscosity is more than 20 cps, a concentration of less than 0.5% of active ingredient is used. In the case where the polymers are not presented in the pure state in the commercial form, a certain amount of alcohol or other solvent will frequently be present, the measurement always being carried out for the presence of 0.5 g of active ingredient per 100 g of solution also containing, in this case, a certain amount of a solvent other than water. In the case of anionic polymers which are insoluble or sparingly soluble in water, these are 100% neutralised with 2-amino-2-methylpropan-1-ol. This solution is then subjected to the Ross Miles test referred to above.

For measuring the density, each 0.5% strength solution of polymer is packaged in an aerosol can which is an aluminium can made in one piece with a pointed neck (45×128), having a Precision P73 valve without a dip tube and having an axial spray button with a conical cup (021550). This aerosol can is filled with 90 g of 0.5% strength solution of polymer and 10 g of the propellant gas Freon F12 or dichlorodifluoromethane.

The test is carried out 24 hours after pressurisation of the aerosols in a conditioned room at 20°±1° C., the equipment and the sample being at this same temperature. A cylindrical cup is weighed empty (its weight is P1) and then filled directly with the foam produced by the aerosol. Each aerosol can is shaken well, before use, so as to emulsify the propellant gas F 12.

For a uniform distribution of the foam in the cup, the aerosols are used with the head downwards and with a uniform rotating motion.

As soon as the expansion of the foam has ended, the latter is immediately and rapidly levelled off with the aid of a wide spatula and the cup is weighed again (its weight is P2).

The density of the foam is determined according to the following formula:

$$\text{density at } 20° \text{ C.} = (P2 - P1)/V$$

(V being the volume of the cup). Three determinations are carried out for each polymer, the value used being the average value of these determinations (in g/cm³).

The solvent medium used for the compositions according to the invention must permit the formation of an unstable foam on contact with the hair, after expansion of the composition in the open air.

This solvent medium preferably consists of water and can optionally contain cosmetically acceptable solvents such as monoalcohols, such as alkanols having 1 to 8 carbon atoms, like ethanol, isopropanol, benzyl alcohol and phenylethyl alcohol; polyalcohols, such as alkylene glycols, like ethylene glycol, propylene glycol and glycerol; glycol ethers, such as mono-, di- and triethylene glycol monoalkyl ethers, like ethylene glycol monoethyl ether and diethylene glycol monoethyl ether; esters, like the acetate of ethylene glycol monomethyl ether and the acetate of ethylene glycol monoethyl ether; and fatty acid esters of a lower alcohol, such as isopropyl myristate or palmitate, used singly or in a mixture. If present, these solvents must make it possible to obtain a foam which satisfies the criterion for the foaming polymers mentioned above. In particular, the foam height of the solution, according to the Ross Miles test, must be more than 1 cm and the density of the resulting foam of the pressurised solution must be less than 0.4 and preferably less than 0.25 g/cm$^3$.

These results can be obtained, in particular, if the abovementioned monoalcohols are present in amounts which do not exceed 50% and are preferably less than 30% by weight, relative to the total weight of the composition (excluding the propellants), and if the glycol ethers and/or the esters are present in amounts which do not exceed 15% by weight, relative to the total weight of the composition (excluding the propellant).

According to a particular embodiment, it is preferred to use water without another solvent; solvents are added especially if the density of the foam of the pressurised solution of the selected cationic or anionic polymer in water is less than 0.25 g/cm$^3$.

Apart from the cationic polymer and the anionic polymer, the composition can also contain adjuvants which are normally used in cosmetics and which do not in themselves have foaming ability, such as dyestuffs which can serve to colour the composition itself or the hair, preservatives, sequestering agents, alkalising or acidifying agents, perfumes, silicones, treatment agents or electrolytes such as namely alcali metal salts.

Hair dyestuffs which may be mentioned are direct dyestuffs, such as azo dyestuffs, anthraquinone dyestuffs, nitrobenzene dyestuffs, indoamines, indoanilines and indophenols, or the leuco-derivatives of these compounds, and also diphenylmethanes and triarylmethanes.

The pH of these solutions is generally 2 to 12 and preferably 5 to 9.

The concentration of the polymers is suitably 0.01 to 10% (by weight). If the composition is intended more particularly for use as a foam, the application of which is not followed by rinsing, it is desirable to use concentrations of cationic polymer of 0.01% to 5% and preferably 0.1 to 3% and concentrations of anionic polymer of 0.01% to 5% and preferably 0.1 to 3%

According to a first embodiment of the invention, it is possible to use a foaming cationic polymer which satisfies the tests indicated above. The polymers mentioned above, which satisfy the tests, are preferably:

quaternised or unquaternised vinylpyrrolidone/dialkylaminoalkyl acrylate or methacrylate copolymers, such as those described more particularly in French Pat. No. 2,077,143, cellulose ether derivatives containing quaternary ammonium groups, such as those described in French Pat. No. 1,492,597, and cationic cellulose derivatives, and the cationic polysaccharides described, in particular, in U.S. Pat. Nos. 3,589,978 and 4,031,307.

It has been possible to obtain particularly valuable results using the cationic polymers sold under the names copolymer 845, CAFQUAT 734 and GAFQUAT 755 by GENERAL ANILINE, the polymers sold under the name J.R. 125, J.R. 400, L.R. 400 and L.R. 30 M by UNION CARBIDE, and those sold under the names CELQUAT L 200 and CELQUAT H. 100 by National STARCH, the polymers sold under the name Jaguar C13S by MEYHALL and those sold under the name COSMEDIA GUAR C261 by BASF.

The anionic polymers which are more particularly used with these foaming cationic polymers are chosen, in a preferred embodiment, from polymers comprising crotonic acid, acrylic or methacrylic acid or sulphonic acid units, such as, more particularly, vinyl acetate/crotonic acid polymers optionally grafted onto a polyethylene glycol, the acrylic copolymers sold under the name ULTRAHOLD 8 by CIBA GEIGY, polymethacrylates, such as the product sold under the name DARVAN No. 7 by Van der Bilt, polyvinylsulphonates, and sodium salts of polyhydroxycarboxylic acids, sold by HENKEL under the name HYDAGEN F.

According to a second embodiment, it is possible to use a foaming anionic polymer with any one of the cationic polymers comprising a large number of primary, secondary, tertiary and/or quaternary amine units. The anionic polymer should in this case satisfy the foam height test according to the Ross Miles method, and the density test, both defined above.

The anionic polymers defined above which give particularly noteworthy results in this embodiment of the invention are from groups A, B, C and D and also polyacrylamides comprising the carboxylate groups defined above.

In this respect, there may be mentioned, in particular, the products sold under the name resin 26-13-14 or 28-13-10 by National Starch, the resins sold under the name ARISTOFLEX A or RESIN TV 242 by HOECHST, the product sold under the name resin 28-29-30 by National Starch, the products sold under the name VERSICOL E or VERSICOL K by ALLIED COLLOID, the product sold under the name ULTRAHOLD 8 by CIBA GEIGY, the products sold under the name RETEN 421, 423 or 425 by HERCULES, the products sold under the name GANTREZ AN 119, 139, 149 and 169, GANTREZ ES 225, 335, 425 and 435 and GANTREZ S95 by GENERAL ANILINE, the product sold under the name EMA 1325 by MONSANTO and the product sold under the name CYANAMER A370 by American CYANAMID.

More particularly preferred associations of the foaming anionic polymers with cationic polymers are the associations with, as cationic polymer, the polymers derived from cationic cellulose, of group 2, cyclic polymers of group 9, cationic polymers of group 5, poly(quaternary ammonium) compounds of group 10, vinylpyrrolidone/dialkylaminoalkyl acrylate or methacrylate copolymers of group 1, and quaternary cationic polymers based on vinylpyrrolidone and on vinylimidazole, such as the polymer sold under the name LUVIQUAT FC 905 by BASF.

According to another preferred embodiment, the foaming cationic polymers are advantageously associated with the preferred foaming anionic polymers described above.

The propellant gases used to pressurise the compositions should be present in proportions which do not exceed 25% and preferably 15%, relative to the total weight of the composition. Propellant gases which can be used include carbon dioxide, nitrogen, nitrous oxide, volatile hydrocarbons, such as butane, isobutane, propane and mixtures thereof, and non-hydrolysable chlorinated and/or fluorinated hydrocarbons, such as those sold under the name FREON by Du Pont de Nemours, in particular the fluorochlorohydrocarbons, such as dichlorodifluoromethane or Freon 12, and dichlorotetrafluoroethane or Freon 114. These propellants can be used singly or in combination; a mixture of Freon 114/12 in proportions from 40:60 to 80:20 may be mentioned in particular.

The present invention also provides a process for the preparation of a foam based on cationic and anionic polymers, which is unstable on contact with the hair, characterised in that this foam is obtained from a composition such as defined above and pressurised in an aerosol device.

The invention also provides the foam thus formed, which is essentially characterised in that it has a density of less than 0.4 and preferably of less than 0.25, and in that it is unstable, that is to say that it disappears very rapidly on contact with the hair after messaging. The disappearance time should be less than 1 minute and preferably less than 30 seconds.

This foam is furthermore characterised in that it comprises cationic and anionic polymers such that at least one of the cationic or anionic polymers satisfies the tests defined above, in an aqueous medium.

This invention also provides a process for the treatment of the hair, which consists in applying a composition as defined above to the hair, in the form of a foam, from an aerosol device.

This application may or may not be followed by rinsing. If this application is not followed by rinsing, it is possible, in particular, to use the foam after shampooing, perming, straightening, colouring or bleaching, or as a finishing product after any hair treatment.

If the application is followed by rinsing, the composition is applied to the hair for, say, a few (2 or 3) minutes to 15 minutes, and the hair is then rinsed with water.

The following Examples further illustrate the present invention. Unless indicated otherwise, all the amounts of polymers are expressed as active ingredient.

EXAMPLE 1

The following composition is prepared:

| Aristoflex A | 2 g |
|---|---|
| Merquat 100 | 1 g |
| Lactic acid q.s.p. | pH = 3 |
| Water q.s.p. | 100 g |

This composition is packaged as an aerosol by introducing 90 g of the composition, together with 10 g of Freon F12, into an aluminium can made in one piece.

The density of the foam obtained is 0.16 g/cm$^3$.

When applied to washed hair, and after massaging, the foam disappears after 30 seconds.

The wet hair impregnated with the composition is easy to comb out and is soft to the touch, and the dried hair has a good hold.

EXAMPLE 2

The following composition is prepared:

| Gantrez ES 425 | 1.0 g |
|---|---|
| Celquat L 200 | 0.5 g |
| 2-Amino-2-methylpropan-1-ol q.s.p. | pH = 6 |
| Water q.s.p. | 100 g |

The anionic polymer GANTREZ ES 425, at a concentration of 0.5% in water, gives a foam height of 5 cm, according to the Ross Miles test, and the average density is 0.13 g/cm$^3$.

90 g of this composition are packaged, together with 10 g of Freon F12, in an aluminium can made in one piece.

The foam formed by the device is applied to the hair by hand and disappears as soon as the hair has been impregnated.

The hair impregnated in this way is soft to the touch and easy to comb out. The dried hair is shiny.

The average density of the foam obtained is 0.07 g/cm$^2$.

EXAMPLE 3

The following composition is prepared:

| Quadramer 5 | 2.0 g |
|---|---|
| Polymer P1 | 0.5 g |
| 2-Amino-2-methylpropan-1-ol q.s.p. | pH = 9.5 |
| Ethyl alcohol q.s.p. | 15° strength |
| Perfume | 0.2 g |
| Water q.s.p. | 100 g |

This composition is packaged in an aluminium can made in one piece, in the presence of Freon F12, in the proportions of 90 g of composition for 10 g of propellant.

When applied to the hair, this pressurised composition gives rise to the formation of a foam which disappears after the hair has been impregnated.

The treated and dried hair is soft to the touch and easy to comb out.

EXAMPLE 4

The following composition is prepared:

| Versicol E13 | 2.0 g |
|---|---|
| Polymer P2 | 0.5 g |
| 2-Amino-2-methylpropan-1-ol q.s.p. | pH = 9 |
| Water q.s.p. | 100 g |

This composition is pressurised in an aerosol device in proportions of 95 g of composition for 5 g of a mixture of alkanes having an intrinsic vapour pressure of 3.2±0.2 bars at 20° C.

This composition gives rise to the formation, in the open air, of a foam having an average density of 0.1 g/cm$^3$. When applied to the hair, it disappears very rapidly and the treated and dried hair has a good hold and is shiny.

EXAMPLE 5

The following composition is prepared:

| Aristoflex A | 2.5 g |
|---|---|
| Gafquat 755 | 0.5 g |
| Triethanolamine q.s.p. | pH = 8 |
| Ethyl alcohol q.s.p. | 15° strength |
| Perfume and dyestuffs | q.s. |
| Water q.s.p. | 100 g |

By packaging this composition as in Example 1, the formation of a mild foam is observed, which disappears on contact with the hair.

The treated hair is soft to the touch and has a good hold.

EXAMPLE 6

The following composition is prepared:

| | |
|---|---|
| Aristoflex A | 2 g |
| Luviquat FC 905 | 1 g |
| Monoethanolamine q.s.p. | pH = 8 |
| Water q.s.p. | 100 g |

This composition, packaged in an aerosol device as described in Example 4, makes it possible to obtain an unctuous foam which makes the treated hair soft and easy to comb out.

EXAMPLE 7

The following composition is prepared:

| | |
|---|---|
| Gafquat 734 | 0.5 g |
| Aristoflex A | 1.0 g |
| 2-Amino-2-methylpropan-1-ol q.s.p. | pH = 8.6 |
| Water q.s.p. | 100 g |

This composition is pressurised under the same conditions as those described in Example 2. When applied to the hair, it disappears rapidly and gives the dried hair a good hold after shaping.

EXAMPLE 8

The following composition is prepared:

| | |
|---|---|
| Gafquat 734 | 1 g |
| Aristoflex A | 1 g |
| Ethyl alcohol q.s.p. | 25° strength |
| 2-Amino-2-methylpropan-1-ol q.s.p. | pH = 8 |
| Water q.s.p. | 100 g |

This composition is pressurised under the same conditions as described in Example 4. The resulting foam has an average density of 0.08 g/cm$^3$.

The treated hair is soft to the touch and easy to comb out.

EXAMPLE 9

The following composition is prepared:

| | |
|---|---|
| Celquat L 200 | 1.0 g |
| Hydagen F | 0.5 g |
| Perfume | 0.1 g |
| Water q.s.p. | 100 g |

This composition is packaged in the manner described in Example 1.

The resulting foam disappears very rapidly on contact with the hair and gives it softness, shine and a good hold.

EXAMPLE 10

The following composition is prepared:

| | |
|---|---|
| Celquat L 200 | 0.5 g |
| Ultrahold 8 | 0.5 g |
| Ethyl alcohol q.s.p. | 10° strength |
| Water q.s.p. | 100 g |

This composition is pressurised in an aluminium container, using, as the propellant gas, a mixture of Freon F12 and Freon F114 in proportions of 70/30. 90 g of composition for 10 g of propellant gas mixture are introduced into the container.

This gives a foam having an average density of 0.08 g/cm$^3$.

When applied to the hair, and after massaging, it disappears in less than 30 seconds.

The dried hair is soft to the touch and easy to comb out and has a good hold.

EXAMPLE 11

The following composition is prepared:

| | |
|---|---|
| Gafquat 734 | 1 g |
| Aristoflex A | 1 g |
| Ethylene glycol monomethyl ether | 5 g |
| 2-Amino-2-methylpropane-1,3-diol q.s.p. | pH = 8.5 |
| Perfume and dyestuffs | qs |
| Water q.s.p. | 100 g |

It is pressurised as indicated in Example 1.

When applied to the hair, the foam disappears rapidly and gives it softness, ease of comb-out and hold.

EXAMPLE 12

The following composition is prepared:

| | |
|---|---|
| Gafquat 755 | 1.5 g |
| Darvan 7 | 3.0 g |
| Water q.s.p. | 100 g |

This composition is packaged as described in Example 1.

When applied to the hair, a uniform distribution and a good comb-out are obtained.

EXAMPLE 13

The following composition is prepared:

| | |
|---|---|
| Celquat L 200 | 0.5 g |
| Sodium polyvinylsulphonate | 0.5 g |
| Water q.s.p. | 100 g |

The composition prepared in this way is packaged as described in Example 1.

The foam which is formed has an average density of 0.09 g/cm$^3$ and it is mild and disappears rapidly on contact with the hair.

The treated hair is soft to the touch and easy to comb out and has a good hold.

EXAMPLE 14

The following composition is prepared:

| | |
|---|---|
| Gafquat 734 | 1 g |
| Sodium polyvinylsulphonate | 2 g |
| Ethyl alcohol q.s.p. | 10° strength |
| Water q.s.p. | 100 g |

By packaging it as described in Example 1, the results observed are similar to those indicated in Example 13.

EXAMPLE 15

The following composition is prepared:

| | |
|---|---|
| Celquat L 200 | 1.0 g |
| Resin 28.29.30 | 0.5 g |
| 2-Amino-2-methylpropan-1-ol q.s.p. | pH = 9 |
| Ethyl alcohol q.s.p. | 5° strength |

This composition is packaged in the manner described in Example 1.

The foam which is formed has an average density of 0.11 g/cm$^3$ and disappears rapidly on contact with the hair.

The uniformly treated hair is shiny and easy to comb out and has a good hold.

EXAMPLE 16

The following composition is prepared:

| Amphomer | 1 g |
|---|---|
| Celquat L 200 | 0.5 g |
| 2-Amino-2-methylpropan-1-ol q.s. | pH = 9.2 |
| Water q.s. | 100 g |

This composition is packaged as described in Example 3.

When it is applied to the hair, the foam produced disappears very rapidly after massaging.

The treated hair is soft to the touch and easy to comb out.

EXAMPLE 17

The following composition is prepared:

| Amphomer | 1 g |
|---|---|
| Gafquat 734 | 1 g |
| 2-Amino-2-methylpropan-1-ol q.s. | pH = 9 |
| Water q.s. | 100 g |

The composition is packaged as described in Example 1.

The foam produced disappears rapidly on contact with the hair, and the treated hair is soft to the touch.

EXAMPLE 18

The following composition is prepared:

| Ultrahold 8 | 0.25 g |
|---|---|
| JR 400 | 0.25 g |
| 2-Amino-2-methylpropan-1-ol q.s.p. | pH = 8.5 |
| Water q.s.p. | 100 g |

This composition is packaged as described in Example 1. When applied to the hair, the results observed are similar to those indicated in Example 1.

EXAMPLE 19

The following composition is prepared:

| Aristoflex A | 0.5 g |
|---|---|
| Resin 28.29.30 | 0.5 g |
| Gafquat 755 | 1 g |
| 2-Amino-2-methylpropan-1-ol q.s.p. | pH 9 |
| Ethyl alcohol q.s.p. | 5° strength |
| Water q.s.p. | 100 g |

The composition is packaged as described in Example 4. The foam which is formed in air disappears after 30 seconds, after massaging into the hair. The treated hair is shiny and soft to the touch.

EXAMPLE 20

The following composition is prepared:

| Aristoflex A | 1 g |
|---|---|
| Polymer P1 | 0.5 g |
| Celquat L200 | 0.5 g |
| 2-Amino-2-methylpropan-1-ol q.s.p. | pH 8.5 |
| Water q.s.p. | 100 g |

The composition is packaged as described in Example 1. The foam which is formed in the open air disappears very rapidly after massaging into the hair. The treated hair has a good hold and is soft to the touch.

The average density of the foam formed is 0.11 g/cm$^3$.

EXAMPLE 21

The following composition is prepared:

| Aristoflex A | 1 g |
|---|---|
| Dow Corning 929 cationic emulsion | 0.5 g |
| 2-Amino-2-methylpropan-1-ol q.s.p. | pH 8.5 |
| Water q.s.p. | 100 g |

The composition is packaged as indicated in Example 1.

The average density of the foam which is formed is 0.08 g/cm$^3$. After massaging, the foam disappears into the hair in less than 30 seconds. The treated hair is soft to the touch and has a good hold.

EXAMPLE 22

The following composition is prepared:

| Gantrez ES 425 | 1 g |
|---|---|
| Gafquat 755 | 0.2 g |
| Sodium chloride | 3 g |
| Sodium hydroxide q.s.p | pH 8.6 |
| Perfume | q.s. |
| Dyestuff | q.s. |
| Preservative | q.s. |
| Water q.s.p. | 100 g |

This composition is packaged as described in Example 4. When applied to the hair, the pressurised composition gives rise to the formation of an unctuous foam which disappears very rapidly after massaging into the hair.

After an interval of 5 minutes, the hair is rinsed with water.

The wet hair is soft to the touch and easy to comb out. The dried hair is shiny and has a good hold.

EXAMPLE 23

The following composition is prepared:

| Cyanamer A 370 | 0.5 g |
|---|---|
| JR 400 | 0.5 g |
| Sodium chloride | 2.5 g |
| Hydrochloric acid q.s.p. | pH 8.5 |
| Perfume | q.s. |
| Dyestuff | q.s. |
| Preservative | q.s. |
| Water q.s.p. | 100 g |

This composition is packaged in an aluminium can made in one piece, in the presence of a mixture of Freon 114/12 in proportions of 50/50. 92 g of composition are used for 8 g of propellant.

The foam which is formed in the open air is applied to the hair. After an interval of 10 minutes, the hair is rinsed with water.

The dried hair has a good hold and is soft to the touch.

EXAMPLE 24

The following composition is prepared:

| Polymer P3 | 0.75 g |
|---|---|
| Polymer P1 | 1 g |
| 2-Amino-2-methylpropan-1-ol q.s.p. | pH 9 |
| Perfume | q.s. |
| Dyestuff | q.s. |
| Preservative | q.s. |
| Water q.s.p | 100 g |

The composition is packaged as indicated in Example 23.

The foam which forms in the open air from the pressurised composition is applied to the hair. The foam disappears very rapidly. After an interval of a few minutes, the hair is rinsed with water. The results observed are similar to those of Example 23.

EXAMPLE 25

The following composition is prepared:

| Amphomer | 1 g |
|---|---|
| 2-Amino-2-methylpropan-1-ol q.s.p. | pH 9.5 |
| Versicol E 13 | 1.5 g |
| Perfume, dyestuff and preservative q.s. | |
| Distilled water q.s.p. | 100 g |

The final pH after the addition of the Versicol E 13 is 4.5.

The Amphomer and the 2-amino-2-methylpropan-1-ol are dissolved with distilled water, and the Versicol E 13 is then added.

80 g of the composition are packaged in an aluminium can made in one piece, together with 20 g of a mixture of Freon 11/12 in the proportions of 43/57.

The foam which forms in the open air is applied to the hair and the hair is rinsed with water after an interval of 10 minutes.

In the foregoing examples, the polymers designated by tradenames correspond to the following products:

| Anionic polymers | |
|---|---|
| ARISTOFLEX A | Vinyl acetate/crotonic acid/polyethylene glycol terpolymer sold by HOECHST |
| GANTREZ ES 425 | Monobutyl ester of poly-(methyl vinyl ether/maleic acid), sold by GENERAL ANILINE |
| QUADRAMER 5 | N—tert.-butylacrylamide/acrylamide/ acrylic acid/N—vinylpyrrolidone copolymer sold by AMERICAN CYANAMID |
| VERSICOL E 13' | Mixture of acrylic acid homopolymer and copolymer, having a molecular weight of about 1,000,000, sold by ALLIED COLLOID |
| HYDAGEN F | Sodium salt of polyhydroxycarboxylic acid, sold by HENKEL |
| ULTRAHOLD 8 | Acrylic acid/ethyl acrylate/N—tert.-butylacrylamide terpolymer sold by CIBA GEIGY |
| DARVAN 7 | Sodium polymethacrylate sold by VAN DER BILT |

| -continued | |
|---|---|
| Resin 28.29.30 | Vinyl acetate/crotonic acid/vinyl neodecanoate terpolymer sold by NATIONAL STARCH |
| Cyanamer A.370 | Modified polyacrylamide having a molecular weight of about 200,000 and a specific viscosity of 3.7 ± 0.5, sold by American Cyanamid |
| Polymer P3 | Vinyl acetate/crotonic acid copolymer (90/10). |
| Cationic polymers | |
| MERQUAT 100 | Dimethyldiallylammonium chloride homopolymer having a molecular weight <100,000, sold by MERCK |
| CELQUAT L 200 | Cationic cellulose derivative sold by NATIONAL STARCH |
| POLYMER P1 | Cationic polymer according to Example 1a of French Patent 2,252,840 (polyamino-polyamide resulting from the polycondensation of adipic acid and diethylenetriamine in equimolecular amounts, and crosslinked with epichlorohydrin at a rate of 11 mols of crosslinking agent per 100 amine groups of the polyaminoamide). |
| POLYMER P2 | Polymer corresponding to the formula: |

$$\left[ \begin{array}{cc} \overset{CH_3}{\underset{C_8H_{17}}{\overset{|}{N_\oplus}}}-(CH_2)_3-\overset{CH_3}{\underset{CH_3}{\overset{|}{N_\oplus}}}-(CH_2)_6 \\ Br^\ominus \qquad\qquad Br^\ominus \end{array} \right]_n$$

| GAFQUAT 755 | Quaternary vinylpyrrolidone copolymer having a molecular weight of 1,000,000, marketed by GENERAL ANILINE |
|---|---|
| LUVIQUAT FC 905 | Quaternary cationic polymer possessing units as follows: |

| vinylpyrrolidone | 5% |
|---|---|
| vinylimidazole | 95% |
| sold by BASF | |

| GAFQUAT 734 | Quaternary vinylpyrrolidone copolymer having a molecular weight of 100,000, marketed by GENERAL ANILINE |
|---|---|
| DOW CORNING 929 cationic emulsion | Mixture of Amodinethicone, "tallowtrimonium chloride" and Nonoxynol-10 according to the CTFA Cosmetic Ingredient Dictionary, 1977 edition, sold by Dow Corning |
| Amphoteric polymer | |
| AMPHOMER | Octylacrylamide/acrylate/butylaminoethyl methacrylate copolymer sold by National Starch. |

EXAMPLE 26

The following composition is prepared:

| Vinyl acetate/Crotonic acid/4-tertiarybutylvinyl-benzoate terpolymer (65/10/25) | 0.5 g |
|---|---|
| Celquat L 200 | 0.8 g |
| 2-amino-2-methylpropan-1-ol | |
| Perfume | qs |
| Demineralised water | qs |

80 g of this composition is packaged in an aluminium can made in one piece with 20 g of a mixture of Freons 114/12 (45/57).

A foam is obtained which is applied to the hair causing the foam to disappear rapidly and which confers a softness, ease of untangling and hold on the hair.

We claim:

1. A cosmetic foamable composition which is suitable for application to the hair and which forms an unstable foam on contact with the hair when expelled from an aerosol container by means of a propellant, said composition comprising a cationic polymer in an amount from about 0.01% to about 5% by weight of the composition, said cationic polymer containing one or more primary, secondary, tertiary or quaternary amine groups or a mixture thereof and having a molecular weight of 500 to 5,000,000; an anionic polymer in an amount from about 0.01% to 5% by weight of the composition, said anionic polymer containing a plurality of sulphonic, carboxylic or phosphoric acid groups and having a molecular weight of 500 to 5,000,000; and an aqueous solvent medium; at least one of said cationic and anionic polymers (i) when in solution in water produces, according to the Ross Miles test carried out at 20 degrees C., a foam height of more than 1 cm, and (ii) when in solution in water and after pressurization of the solution produces a foam having a density of less than 0.25 g/cm$^3$; said cationic and anionic polymers being polymers which together foam in an aqueous solvent medium in the absence of a surface active agent possessing foaming properties to produce a foam having a density of less than 0.25 g/cm$^3$ and disappearing in less than 1 minute after application to the hair and massaging; and said unstable foam produced by said composition having a density of less than 0.25 g/cm$^3$ and disappearing very rapidly after application to the hair and massaging.

2. A composition according to claim 1, in which the solvent medium consists of water.

3. The composition of claim 1, wherein said composition contains less than 30% by weight of the composition of a monoalcohol.

4. The composition of claim 1, wherein said composition contains less than 15% by weight of the composition of a glycol ether, glycol ester or fatty acid ester of a lower alcohol.

5. The composition of claim 1, wherein said composition contains a polyalcohol.

6. In a cosmetic composition suitable for application to the hair in a form to be expelled from an aerosol container by means of a propellant containing a cationic polymer having one or more primary, secondary, tertiary, or quaternary amine groups or mixtures thereof and having a molecular weight of 500 to 5,000,000, an anionic polymer containing a plurality of sulphonic, carboxylic, or phosphoric acid groups and having a molecular weight of 500 to 5,000,000, and an aqueous solvent medium, wherein the improvement comprises a composition which produces an unstable foam on contact with the hair when expelled from said aerosol container by means of said propellant wherein:

(a) at least one of said cationic and anionic polymers (i) when in solution in water produces, according to the Ross Miles test conducted at 20 degrees C., a foam height of more than 1 cm, and (ii) when in solution in water and after pressurization of the solution produces a foam having a density of less than 0.25 g/cm$^3$;

(b) said aqueous solvent medium being water, or a mixture of water and an amount of monoalcohol which is less than 30% by weight of the composition, or a mixture of water and polyalcohol, glycol ether, glycol ester or a fatty acid ester of a lower alcohol;

(c) said cationic and anionic polymers being polymers which together foam in an aqueous solvent medium in the absence of a surface active agent possessing foaming properties to produce a foam having a density of less than 0.25 g/cm$^3$ and disappearing in less than 1 minute after application to the hair and massaging; and (d) the foam produced by said foamable composition is unstable, has a density of less than 0.25 g/cm$^3$ and disappears very rapidly after application to the hair and massaging.

7. The composition of claim 6, wherein said polymer when in solution in water produces, according to the Ross Miles test conducted at 20° C., a foam height of more than 1 cm, and in solution in water and after pressurization of the solution produces a foam having a density of less than 0.25 g/cm$^3$, is a cationic polymer.

8. The composition of claim 1 or 7, wherein said cationic polymer is selected from the group consisting of:

(1) a quaternised or unquaternised vinylpyrrolidone/-dialkylaminoalkyl acrylate or methacrylate copolymer;
(2) a cellulose ether derivative containing quaternary ammonium groups,
(3) a quaternary cellulose derivative; and
(4) a cationic polysaccharide.

9. The composition of claim 6 wherein said polymer which, in solution in water produces, according to the Ross Miles test conducted at 20° C., a foam height of more than 1 cm, and in solution in water and after pressurization of the solution produces a foam having a density of less than 0.25 g/cm$^3$, is an anionic polymer.

10. The composition of claim 6, wherein said composition contains less than 30% by weight of the composition of a monoalcohol.

11. The composition of claim 6, wherein said composition contains less than 15% by weight of the composition of a glycol ether, glycol ester or fatty acid ester of a lower alcohol.

12. The composition of claim 6, wherein said composition contains a polyalcohol.

13. The composition of claim 6, wherein said foam disappears in less than one minute after application to the hair and massaging.

14. A composition according to claim 6, in which the solvent medium consists of water.

15. A composition according to claim 6, in which the cationic polymer is:

(1) a quaternised or unquaternised vinylpyrrolidone/-dialkylaminoalkyl acrylate or methacrylate copolymer,
(2) a cellulose ether derivative containing quaternary ammonium groups,
(3) a quaternary cellulose derivative,
(4) a cationic polysaccharide,
(5) a cationic polymer comprising units of the formula —A—Z—A—Z (I), in which A denotes a radical containing two amino groups, and Z denotes the symbol B or B'; B and B', which are identical or different, denote a linear or branched alkylene radical which is unsubstituted or substituted by one or more hydroxyl groups and can also contain one or more oxygen, nitrogen or sulphur atoms and/or 1 to 3 aromatic and/or heterocyclic rings;

or units of the formula: —A—$Z_1$—A—$Z_1$— (II), in which A is as defined above and $Z_1$ denotes the symbol $B_1$ or $B'_1$ while denoting $B'_1$ at least once; $B_1$ denoting a linear or branched alkylene or hydroxyalkylene radical and $B'_1$ denoting a linear or branched alkylene radical which is unsubstituted or substituted by one or more hydroxyl radicals and is interrupted by one or more chain nitrogen atoms, the nitrogen atom being substituted by an alkyl chain or an alkyl chain which contains a chain oxygen atom or contains one or more hydroxyl groups; or an alkylation product of a said polymer of formula (I) or (II), with an alkyl or benzyl halide or lower alkyl tosylate or mesylate, or an oxidation product, of a said polymer of formula (I) or (II), (6) a polyamino-polyamide, (7) a crosslinked polyamino-polyamide which is:

(a) a crosslinked polyamino-polyamide or alkylated, crosslinked polyamino-polyamide obtained by crosslinking a polyamino-polyamide prepared by the polycondensation of an acid compound with a polyamine, the crosslinking agent being an epihalogenohydrin, diepoxide, dianhydride, unsaturated anhydride or a bis-unsaturated derivative, the crosslinking agent being used in an amount from 0.025 to 0.35 mol per amine group of the polyaminoamide;

(b) a crosslinked polyamino-polyamide obtained by crosslinking a polyamino-polyamide as defined above, with a crosslinking agent which is:

I—a bis-halogenohydrin, bis-azetidinium compound, bis-halogenoacyl-diamine or bis-(alkyl halide), II—an oligomer obtained by reacting a compound of group I or an eiphalogenohydrin, diepoxide or bis-unsaturated derivative, with a difunctional compound which is reactive towards said compound, or III—a quaternisation product of a compound of group I and oligomer of group II, containing tertiary amine groups which can be totally or partially alkylated, with an alkylating agent, the crosslinking being used in an amount from 0.025 to 0.35 mol per amine group of the polyamino-polyamide; or (c) a polyamino-polyamide derivative resulting from the condensation of a polyalkylene-polyamine with a polycarboxylic acid, followed by alkylation by a difunctional agent, (8) a polymer obtained by reacting a polyalkylene-polyamine containing two primary amine groups and at least one secondary amine group, with a dicarboxylic acid which is diglycolic acid or a saturated aliphatic dicarboxylic acid having 3 to 8 carbon atoms, the molar ratio of the polyalkylene-polyamine to the dicarboxylic acid being from 0.8:1 to 1.4:1, and the resulting polyamide being reacted with epichlorohydrin in a molar ratio of epichlorohydrin to the secondary amine groups of the polyamide from 0.5:1 to 1.8:1, (9) a cyclic polymer containing units corresponding to the formula (III) or (III')

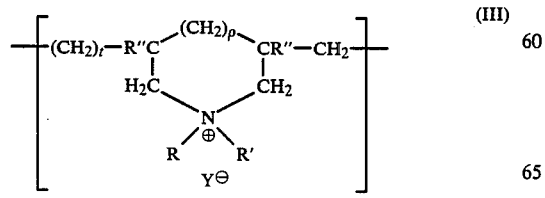

(III)

or

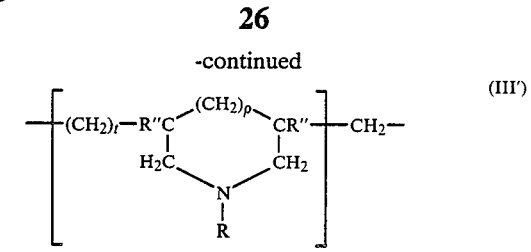

(III')

in which $p$ and $t$ are equal to 0 to 1 such that $p+t=1$, R'' denotes hydrogen or methyl, R and R' independently of one another denote an alkyl group having 1 to 22 carbon atoms, a hydroxyalkyl group, or a lower amidoalkyl group, or R and R' together denote with the nitrogen atom to which they are attached, a heterocyclic group and $Y^{\ominus}$ is an anion,

(10) a poly-(quaternary ammonium) compound of the formula:

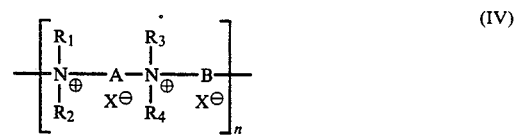

(IV)

in which $R_1$ and $R_2$, and $R_3$ and $R_4$, which are identical or different, represent an aliphatic, alicyclic or arylaliphatic radical containing a maximum of 20 carbon atoms, or a lower hydroxyaliphatic radical, or alternatively $R_1$ and $R_2$, and $R_3$ and $R_4$, together or separately form, with the nitrogen atoms to which they are attached, a heterocyclic ring optionally containing a second hetero-atom other than nitrogen, or $R_1$, $R_2$, $R_3$ and $R_4$ represent a group

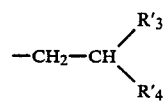

R'$_3$ denoting hydrogen or lower alkoxy and R'$_4$ denoting

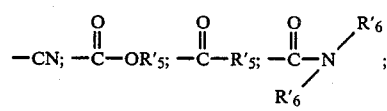

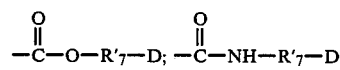

R'$_5$ denoting lower alkyl, R'$_6$ denoting hydrogen or lower alkyl, R'$_7$ denoting alkylene and D denoting a quaternary ammonium group; A and B independently represent a polymethylene group containing from 2 to 20 carbon atoms, which can be linear or branched and saturated or unsaturated and can contain, one or more chain aromatic rings, or one or more groups —CH$_2$—Y—CH$_2$—, Y denoting O, S,

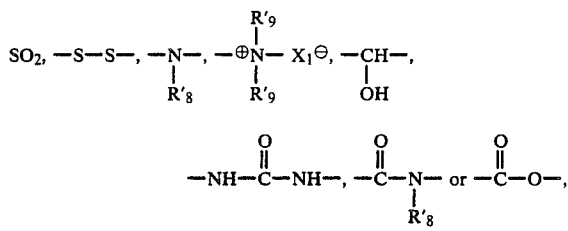

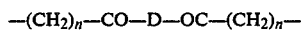

$X_1^\ominus$ denoting an anion derived from a mineral or organic acid, $R'_8$ denoting hydrogen or lower alkyl and $R'_9$ denoting lower alkyl, or A and $R_1$ and $R_3$ form a piperazine ring with the two atoms to which they are attached; or, additionally, if A denotes a linear or branched, saturated or unsaturated alkylene or hydroxyalkylene radical, B can also denote a group:

$$-(CH_2)_n-CO-D-OC-(CH_2)_n-$$

in which D denotes:

(a) a glycol radical of the formula $-O-Z-O-$, in which Z denotes a linear or branched hydrocarbon radical or a group corresponding to the formulae

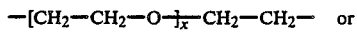

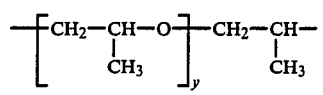

in which x and y independently denote an integer from 1 to 4;

(b) a bis-secondary diamino radical;

(c) a bis-primary diamino radical of the formula: $-N-H-Y-NH-$, in which Y denotes a linear or branched hydrocarbon radical or the radical $-CH_2-CH_2-S-S-CH_2-CH_2-$; or (d) a ureylene group of the formula $-N-H-CO-NH-$; n is such that the molecular weight of the compound is from 1,000 to 100,000; and $X^\ominus$ denotes an anion,

(11) a homopolymer or copolymer derived from acrylic or methacrylic acid and containing at least one unit:

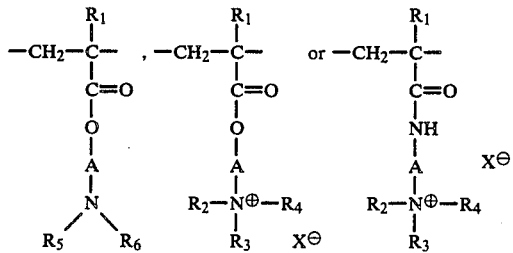

in which $R_1$ is H or $CH_3$, A is a linear or branched alkyl group having up to 6 carbon atoms or a hydroxyalkyl group having 1 to 4 carbon atoms, $R_2$, $R_3$ and $R_4$, which are identical or different, denote an alkyl group having 1 to 18 carbon atoms or a benzyl group, $R_5$ and $R_6$ independently denote H or alkyl having 1 to 6 carbon atoms and $X^\ominus$ denotes a methosulphate of halide anion,

(12) a quaternary vinylpyrrolidone/vinylimidazole copolymer,

(13) a polyalkyleneimine,

(14) a polymer containing one or more chain vinylpyridine or vinylpyridinium units,

(15) a condensate of a polyamine and epichlorohydrin,

(16) a poly-(quaternary ureylene), or

(17) a cationic silicone polymer.

16. A composition according to claim 15, in which the polymer which foams is cationic and is a polymer of groups (1), (2), (3) or (4) as defined in claim 15.

17. A composition according to claim 6, in which the anionic polymer is:

a polymer containing units derived from an unsaturated monocarboxylic or dicarboxylic acid of the formula:

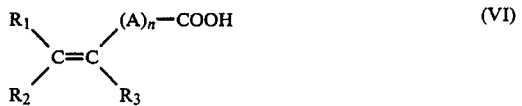

in which n is 0 or an integer from 1 to 10, A denotes a methylene group, optionally joined to the carbon atom of the unsaturated group, or to the adjacent methylene group where n is greater than 1, via a hetero-atom, $R_1$ denotes a hydrogen atom or a phenyl or benzyl group, $R_2$ denotes a hydrogen atom, a lower alkyl group or a carboxyl group and $R_3$ denotes a hydrogen atom, a lower alkyl group, a group $-CH_2-COOH$ or a phenyl or benzyl group; or a polymer comprising units derived from a sulphonic acid.

18. A composition according to claim 6, which contains an amphoteric polymer in addition to a true cationic or anionic polymer which foams.

19. A composition according to claim 6, which contains one or more non-foaming cosmetic adjuvants.

20. A composition according to claim 6, which has a pH of 2 to 12.

21. A composition according to claim 6, in which the polymers are present in a concentration of 0.1 to 3% by weight.

22. A composition according to claim 6, which is pressurised with, as propellant gas, carbon dioxide, nitrogen, nitrous oxide, butane, isobutane, propane or a mixture thereof or a non-hydrolysable chlorinated and-/or fluorinated hydrocarbon.

23. A composition according to claim 1 or 6 wherein the anionic polymer is:

(i) a vinyl acetate/crotonic acid/polyethylene glycol polymer, (ii) a monobutyl ester of poly(methyl vinyl ether/-maleic acid, (iii) an acrylic acid/ethylacrylate/N-tertio butylacrylamide, (iv) a vinylacetate/crotonic acid/vinylneodecanoate, (v) a vinyl acetate/crotonic acid, or (vii) a polyacrylamide containing carboxylate groups.

24. A cosmetic foamable composition which is suitable for application to the hair and which forms an unstable foam on contact with the hair when expelled from an aerosol container by means of a propellant, said composition comprising: a cationic polymer in an amount from about 0.01% to about 5% by weight of the composition, said cationic polymer containing one or more primary, secondary, tertiary or quaternary amine groups or a mixture thereof and having a molecular weight of 500 to 5,000,000; an anionic polymer in an amount from about 0.01% to 5% by weight of the composition, said anionic polymer containing a plurality of sulphonic, carboxylic or phosphoric acid groups and having a molecular weight of 500 to 5,000,000; and an aqueous solvent medium; said aqueous solvent medium being water, or a mixture of water and a monoalcohol in which the monoalcohol is less than 30% by weight of the composition, or a mixture of water and glycol ether, glycol ester or fatty acid ester of a lower alcohol in which the ether or ester is less than 15% by weight of the composition; at least one of said cationic and anionic polymers (i) when in solution in water produces, according to the Ross Miles test carried out at 20 degrees C., a foam height of more than 1 cm, and (ii) when in solution in water and after pressurization of the solution produces a foam having a density of less than 0.25 g/cm$^3$; said cationic and anionic polymers being polymers which together foam in an aqueous solvent medium in the absence of a surface active agent possessing foaming properties to produce a foam having a density of less than 0.25 g/cm$^3$ and disappearing in less than 1 minute after application to the hair and massaging; said unstable foam produced by said composition having a density of less than 0.25 g/cm$^3$ and disappearing very rapidly after application to the hair and massaging.

25. A cosmetic composition under pressure which forms when expelled an unstable foam on contact with hair which comprises a cationic polymer selected from the group consisting of a cationic silicone polymer and a quaternary cellulose derivative and an anionic polymer, such that at least one said polymer foams in an aqueous solvent medium, in an aqueous solvent medium which is water, or a mixture of water and an amount of a monoalcohol which is less than 30% by weight of the composition, or a mixture of water and polyalcohol, glycol ether, glycol ester or fatty acid ester of a lower alcohol, such that when released to the atmosphere the composition forms an unstable foam on contact with the hair, wherein said cationic polymer has a molecular weight of 500 to 5,000,000; wherein said anionic polymer is one containing a plurality of sulphonic, carboxylic or phosphoric acid groups and has a molecular weight of 500 to 5,000,000; and wherein the polymer which foams is one which, at a concentration of 0.5% by weight in an aqueous solution, gives a foam height of more than 1 cm, according to the Ross Miles test modified as regards to the temperature and carried out at 20 degrees C., and which when released under pressure to the atmosphere, gives a foam having a density not exceeding 0.25 g/cm$^3$.

26. A cosmetic composition under pressure which forms when expelled an unstable foam on contact with hair which comprises a polymer containing one or more cationic groups and an anionic polymer selected from the group consisting of a copolymer of vinylacetate/crotonic acid/vinyl ester of an α or β-cyclic carboxylic acid or a copolymer of methacrylic acid and methacrylic acid ester, such that at least one said polymer foams in an aqueous solution which is water, or a mixture of water and a monoalcohol which is less than 30% by weight of the composition, or a mixture of water and polyalcohol, glycol ether, glycol ester or fatty acid ester of a lower alcohol, such that when released to the atmosphere the composition forms an unstable foam on contact with the hair, wherein said polymer containing one or more cationic groups is a cationic polymer containing a primary, secondary, tertiary or quaternary amine group or a mixture thereof and having a molecular weight of 500 to 5,000,000; wherein said anionic polymer has a molecular weight of 500 to 5,000,000; and wherein the polymer which foams is one which, at a concentration of 0.5% by weight in an aqueous solution, gives a foam height of more than 1 cm, according to the Ross Miles test modified as regards the temperature and carried out at 20 degrees C., and which, when released under pressure to the atmosphere, gives a foam having a density not exceeding 0.25 g/cm$^3$.

27. The composition of claim 26 wherein said anionic polymer is a copolymer of vinyl acetate/crotonic acid/vinyl p.tertiobutylbenzoate.

28. In a cosmetic composition suitable for application to the hair in a form to be expelled from an aerosol container by means of a propellant containing a cationic polymer having one or more primary, secondary, tertiary, or quaternary amine groups or mixtures thereof and having a molecular weight of 500 to 5,000,000, an amphoteric polymer which consists of units A and B randomly distributed in the polymer chain, in which A denotes a unit derived from a monomer containing at least one basic nitrogen atom and B denotes a unit derived from an acid monomer containing one or more carboxylic or sulphonic acid groups, or alternatively A and B can denote groups derived from zwitterionic monomers of carboxybetaine, or A and B can denote a cationic polymer chain containing secondary, tertiary or quaternary amine groups, in which at least one of the amine groups carries a carboxylic or sulphonic acid group joined via a hydrocarbon radical, or alternatively A and B form part of a chain of a polymer containing an alpha, beta-dicarboxyethylene unit in which one of the carboxylic acid groups has been reacted with a polyamine containing one or more primary or secondary amine groups, and an aqueous solvent medium, wherein the improvement comprises a composition which forms when expelled from said aerosol container by means of said propellant an unstable foam on contact with the hair wherein:

(a) said cationic polymer (i) when in solution in water produces, according to the Ross Miles test conducted at 20 degrees C., a foam height of more than 1 cm, and (ii) when in solution in water and after pressurization of the solution produces a foam having density of less than 0.25 g/cm$^3$;

(b) said aqueous solvent medium being water, or a mixture of water and an amount of monoalcohol which is less than 30% by weight of the composition, or a mixture of water and polyalcohol, glycol ether, glycol ester or a fatty acid ester of a lower alcohol;

(c) said cationic and amphoteric polymers being polymers which together foam in an aqueous solvent medium in the absence of a surface active agent possessing foaming properties to produce a foam having a density of less than 0.25 g/cm$^3$ and disappearing in less than 1 minute after application to the hair and massaging; and (d) the foam produced by said foamable composition is unstable, has a density of less than 0.25 g/cm$^3$ and disappears very rapidly after application to the hair and massaging.

29. In a cosmetic composition suitable for application to the hair in a form to be expelled from an aerosol container by means of a propellant containing an anionic polymer containing a plurality of sulphonic, carboxylic, or phosphoric acid groups and having a molecular weight of 500 to 5,000,000, an amphoteric polymer which consists of units A and B randomly distributed in the polymer chain, in which A denotes a unit derived from a monomer containing at least one basic nitrogen atom and B denotes a unit derived from an acid monomer containing one or more carboxylic or sulphonic acid groups, or alternatively A and B can denote groups derived from zwitterionic monomers of carboxybetaine, or A and B can denote a cationic polymer chain containing secondary, tertiary or quaternary amine groups, in which at least one of the amine groups carries a carboxylic or sulphonic acid group joined via a hydrocarbon radical, or alternatively A and B form part of a chain of a polymer containing an alpha, beta-dicarboxyethylene unit in which one of the carboxylic acid groups has been reacted with a polyamine containing one or more primary or secondary amine groups, and an aqueous solvent medium, wherein the improvement comprises a composition which forms when expelled from said aerosol container by means of said propellant an unstable foam on contact with the hair wherein:

(a) said anionic polymer (i) when in solution in water produces, according to the Ross Miles test conducted at 20 degrees C., a foam height of more than 1 cm, and (ii) when in solution in water and after pressurization of the solution produces a foam having density of less than 0.25 g/$cm^3$;

(b) said aqueous solvent medium being water, or a mixture of water and an amount of monoalcohol which is less than 30% by weight of the composition, or a mixture of water and polyalcohol, glycol ether, glycol ester or a fatty acid ester of a lower alcohol;

(c) said amphoteric and anionic polymers being polymers which together foam in an aqueous solvent medium in the absence of a surface active agent possessing foaming properties to produce a foam having a density of less than 0.25 g/$cm^3$ and disappearing in less than 1 minute after application to the hair and massaging; and (d) the foam produced by said foamable composition is unstable, has a density of less than 0.25 g/$cm^3$ and disappears very rapidly after application to the hair and massaging.

30. A composition according to claim 9 or 29 in which the anionic polymer is selected from the group consisting of:

(i) a homopolymer of acrylic or methacrylic acid or a salt thereof, (ii) an acrylic acid/acrylamide copolymer, (iii) a crotonic acid/vinyl acetate or vinyl propionate, (iv) a crotonic acid/vinyl acetate or vinyl propionate/allyl or methallyl ester, (v) a crotonic acid/vinyl acetate or vinyl propionate/vinyl ether, (vi) a crotonic acid/vinyl acetate or vinyl propionate/vinyl ester of a saturated linear or branched carboxylic acid with a long hydrocarbon chain of at least 5 carbon atoms, (vii) a crotonic acid/vinyl acetate or vinyl propionate/vinyl, allyl or methallyl ester of an $\alpha$ or $\beta$ cyclic carboxylic acid, (viii) a crotonic acid/vinyl acetate grafted onto polyethylene glycol, (ix) maleic acid or anhydride/vinyl ester, vinyl ether, vinyl halide or phenyl vinyl copolymer and their esters, and (x) polyacrylamide containing carboxylate groups.

31. In a cosmetic composition suitable for application to the hair in a form to be expelled from an aerosol container by means of a propellant containing a cationic polymer, an anionic polymer containing a plurality of sulphonic, carboxylic, or phosphoric acid groups and having a molecular weight of 500 to 5,000,000 and an aqueous solvent medium, wherein the improvement comprises a composition which forms when expelled from said aerosol container by means of said propellant an unstable foam on contact with the hair wherein:

(a) said at least one cationic polymer is a quaternary cellulose polymer (i) when in solution in water produces, according to the Ross Miles test conducted at 20 degrees C., a foam height of more than 1 cm, and (ii) when in solution in water and after pressurization of the solution, produces a foam having a density of less than 0.25 g/$cm^3$;

(b) said aqueous solvent medium being water, or a mixture of water and an amount of monoalcohol which is less than 30% by weight of the composition, or a mixture of water and polyalcohol, glycol ether, glycol ester or a fatty acid ester of a lower alcohol;

(c) said cationic and anionic polymers being polymers which together foam in an aqueous solvent medium in the absence of a surface active agent possessing foaming properties to produce a foam having a density of less than 0.25 g/$cm^3$ and disappearing in less than 1 minute after application to the hair and massaging; and (d) the foam produced by said foamable composition is unstable, has a density of less than 0.25 g/$cm^3$ and disappears very rapidly after application to the hair and massaging.

32. A cosmetic foamable composition which is suitable for application to the hair and which forms an unstable foam on contact with the hair when expelled from an aerosol container by means of a propellant, said composition comprising a cationic polymer in an amount from about 0.01% to about 5% by weight of the composition, said cationic polymer containing one or more primary, secondary, tertiary or quaternary amine groups or a mixture thereof and having a molecular weight of 500 to 5,000,000; an anionic polymer in an amount from about 0.01% to 5% by weight of the composition, and an aqueous solvent medium; at least one of said cationic polymers being a quaternary cellulose polymer which in solution in water produces, according to the Ross Miles test carried out at 20 degrees C., a foam height of more than 1 cm; said cationic polymer producing in solution in water and after pressurization of the solution a foam having a density of less than 0.25 g/$cm^3$; said at least one anionic polymer being an ester of a maleic acid/vinylether copolymer; said cationic and anionic polymers being polymers which together foam in an aqueous solvent medium in the absence of a surface active agent possessing foaming properties to produce a foam having a density of less than 0.25 g/$cm^3$ and disappearing in less than 1 minute after application to the hair and massaging; and said unstable foam produced by said composition having a density of less than 0.25 g/$cm^3$ and disappearing very rapidly after application to the hair and massaging.

33. A foamable composition according to claim 32 further comprising a cationic silicone polymer.

34. A foamable composition according to claim 32 further containing a cationic silicone, and tallow trimonium chloride.

35. A foamable composition according to claim 32 further containing a quaternary vinyl pyrrolidone/-dialkylamino alkyl aacrylate or methacrylate copolymer.

36. A foamable composition according to claim 32, containing in an aqueous medium,
   (i) an ester of a copolymer of vinyl ether/maleic acid,
   (ii) a quaternary cellulose polymer,
   (iii) a quaternary vinylpyrrolidone/dialkylamino alkyl acrylate or methacrylate copolymer;
   (iv) a cationic silicone polymer, and
   (v) a tallow trimonium chloride forming after having been expelled from the aerosol container by means of a propellant an unstable foam disappearing very rapidly after application to the hair and massaging.

37. A hair styling composition which is suitable for application to the hair and which forms an unstable foam on contact with the hair when expelled from an aerosol container by means of a propellant, said composition comprising a cationic polymer in an amount from about 0.01% to about 5% by weight of the composition, said cationic polymer containing one or more primary, secondary, tertiary or quaternary amine groups or a mixture thereof and having a molecular weight of 500 to 5,000,000; an anionic polymer in an amount from about 0.01% to 5% by weight of the composition, said anionic polymer containing a plurality of sulphonic, carboxylic or phosphoric acid groups and having a molecular weight of 500 to 5,000,000; and an aqueous solvent medium; at least one of said cationic and anionic polymers (i) when in solution in water produce, according to the Ross Miles test carried out at 20 degrees C., a foam height of more than 1 cm, and (ii) when in solution in water and after pressurization of the solution produces a foam having a density of less than 0.25 $g/cm^3$; said cationic and anionic polymers being polymers which together foam in a solvent medium in the absence of a surface active agent possessing foaming properties to produce a foam having a density of less than 0.25 $g/cm^3$ and disappearing in less than 1 minute after application to the hair and massaging; and said unstable foam produced by said composition having a density of less than 0.25 $g/cm^3$ and disappearing very rapidly after application to the hair and massaging.

38. Process for the treatment of the hair, which comprises applying thereto at least one foam as defined in claim 6 from an aerosol device.

39. Process according to claim 38 and further comprising rinsing the hair.

* * * * *